US012595472B2

(12) United States Patent
Kline et al.

(10) Patent No.: US 12,595,472 B2
(45) **Date of Patent: *Apr. 7, 2026**

(54) MANNANASE VARIANTS

(71) Applicant: BASF SE, Ludwigshafen (DE)

(72) Inventors: Katie Kline, San Diego, CA (US); Amanda Rae Logue, San Diego, CA (US); Asfia Qureshi, San Diego, CA (US); Cindy Hoang, San Diego, CA (US); Jesper Nielsen, San Diego, CA (US); Mark Miller, San Diego, CA (US); James Garrett Bonner, San Diego, CA (US)

(73) Assignee: BASF SE, Ludwigshafen am Rhein (DE)

( * ) Notice: Subject to any disclaimer, the term of this patent is extended or adjusted under 35 U.S.C. 154(b) by 686 days.

This patent is subject to a terminal disclaimer.

(21) Appl. No.: 17/799,049

(22) PCT Filed: Feb. 12, 2021

(86) PCT No.: PCT/EP2021/053484

§ 371 (c)(1),
(2) Date: Aug. 11, 2022

(87) PCT Pub. No.: WO2021/160820

PCT Pub. Date: Aug. 19, 2021

(65) Prior Publication Data

US 2023/0091704 A1 Mar. 23, 2023

Related U.S. Application Data

(60) Provisional application No. 62/976,823, filed on Feb. 14, 2020.

(51) Int. Cl.
*C12N 9/24* (2006.01)
*C11D 3/386* (2006.01)
*C12N 15/63* (2006.01)

(52) U.S. Cl.
CPC ........ *C12N 9/2488* (2013.01); *C11D 3/38636* (2013.01); *C12N 15/63* (2013.01)

(58) Field of Classification Search
CPC .................................................... C12N 9/2488
See application file for complete search history.

(56) References Cited

FOREIGN PATENT DOCUMENTS

| | | | |
|---|---|---|---|
| EA | 023087 | B1 | 4/2016 |
| EP | 2409981 | A1 | 1/2012 |
| EP | 3385361 | A1 | 10/2018 |
| EP | 3385377 | A1 | 10/2018 |
| RU | 2712877 | C2 | 1/2020 |

OTHER PUBLICATIONS

International Application No. PCT/EP2021/053484, International Search Report and Written Opinion, mailed Jun. 7, 2021.
Broun, et al., "Catalytic plasticity of fatty acid modification enzymes underlying chemical diversity of plant lipids", Science, vol. 282, Issue 5392, Nov. 13, 1998, pp. 1315-1317.
Kumagai, et al., "Molecular insights into the mechanism of thermal stability of actinomycete mannanase", FEBS letters, vol. 590, Issue 17, Jul. 22, 2016, pp. 2862-2869.
Seffernick, et al., "Melamine deaminase and atrazine chlorohydrolase: 98 percent identical but functionally different", Journal of bacteriology, vol. 183, Issue 8, Apr. 15, 2001, pp. 2405-2410.
Whisstock, et al., "Prediction of protein function from protein sequence and structure", Quarterly reviews of biophysics, vol. 36, Issue 3, Aug. 1, 2003, pp. 307-340.
Witkowski, et al., "Conversion of a β-ketoacyl synthase to a malonyl decarboxylase by replacement of the active-site cysteine with glutamine", Biochemistry, vol. 38, Issue 36, Aug. 18, 1999, pp. 11643-11650.
Yampolsky, et al., "The exchangeability of amino acids in proteins", Genetics, vol. 170, Issue 4, Aug. 1, 2005, pp. 1459-1472.

*Primary Examiner* — Yong D Pak
(74) *Attorney, Agent, or Firm* — ArentFox Schiff LLP

(57) ABSTRACT

A mannanase at least 75% identical to SEQ ID NO: 2 or SEQ ID NO: 3, a polynucleotide encoding the mannanase, an expression construct comprising the polynucleotide, and a host cell comprising the polynucleotide or the expression construct.

14 Claims, No Drawings

Specification includes a Sequence Listing.

MANNANASE VARIANTS

CROSS-REFERENCE TO RELATED APPLICATIONS

This is the U.S. national phase of International Application No. PCT/EP2021/053484, filed Feb. 12, 2021, which claims the benefit of U.S. Provisional Patent Application No. 62/976,823, filed on Feb. 14, 2020.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "201910A_Seqlisting", which was created on Aug. 2, 2022 and is 10 kilobytes in size. The subject matter of the Sequence Listing is incorporated herein in its entirety by reference.

This invention relates to variants of mannanase enzyme. The variants are useful in industrial applications wherein degradation or modification of mannan is desired, such as in laundry and cleaning applications, in feed, food, pulp and paper and oil industry. The invention also provides useful mannanases enzymes, polynucleotides encoding these enzymes, enzyme compositions and methods for their production and use.

The main role of hemicelluloses and galactomannans is to function as structural polysaccharide and/or as reserve energy. Besides amylose and amylopectin which are the most widespread storage polysaccharides in plants, there is a diverse group of mannan-based polysaccharides found in seeds, roots, bulbs and tubers of various plants. These include mannans, galactomannans and glucomannans.

Mannans are polysaccharides with a backbone of β-1,4-linked D-mannopyranosyl residues. In most cases the mannans are highly insoluble in water but have high water binding capacity. In contrast to unsubstituted mannans, the galactomannans are water soluble. Due to the complex structural composition of the plant cell wall, microorganisms thriving on decaying plant material must possess a number of different enzymes that are able to hydrolyse these highly polymeric and mostly insoluble materials. The two major endo-acting enzymes involved in degradation of hemicelluloses are beta-mannanase and beta-xylanase. In addition, the exo-acting enzymes beta-mannosidase, alpha-galactosidase and beta-glucosidase are needed for complete degradation of galactoglucomannan.

The main enzyme type participating in the degradation of mannan backbones are endo-1,4-beta-mannanases (EC 3.2.1.78), which hydrolyze the internal glycoside bonds in the mannan backbone. Endo-1,4-β-mannanases (EC 3.2.1.78) are mannan-degrading enzymes which may be called endo-β-1,4-D-mannanase, β-mannanase, or mannanase herein. Since endo-1,4-beta-mannanases (EC 3.2.1.78) degrade the mannan-backbone, mannan-degradation includes the degradation of mannans, galactomannans and/or glucomannans.

The use of mannanase enzymes is widespread in food and feed applications, the detergent, and the pulp and paper industry:

- The use of mannanase enzymes as feed additives has been shown to provide several beneficial effects since mannan is a contributing factor to viscosity of gut contents and it thereby adversely affects the feed digestibility and animal growth rate.

- In the food industry mannanase enzymes are described for the use in the production of instant coffee where the enzyme reduces the viscosity of the coffee extracts due to hydrolysis of the coffee mannan. Further, mannanases are used to produce specific manno-oligomers that are of interest as functional food ingredients such as manno-oligomers with a prebiotic functionality. In such applications plant derived manno-polymers are subjected to hydrolysis by mannanases.
- It is common to use mannanases in the processing and manufacturing fruit juice because it lowers viscosity and improves filtration rate, stability and helps to extract fruit components.
- Detergent use: mannanases facilitate the removal of food and cosmetic derived stains/soils that often comprise mannan containing additives like stabilizers, emulsifiers and thickeners. In a more specific cleaning application mannanases are applied to remove biofilms from surfaces or tubings that need to be free from microbials like pharmaceutical equipment. In this application mannanases are often used in combination with detergents and other enzymes like carbohydrases and proteases.
- Pulp and paper: mannanases are used in the enzyme-aided bleaching of paper pulp. Mannanases are said to complement the action of xylananses.
- Mannanases are applied in the process of oil and gas well stimulation by hydraulic fracturing. Mannanases reduce viscosity of a guar solution that is applied in the process.
- Mannanases are used in the controlled release of drugs or other material from matrices that are composed of cross-linked galactomannans.

Activity under application conditions is a critical parameter for many industrially applied enzymes, since these enzymes often tend to be insufficiently active under application conditions. Therefore, it was an objective of the present invention to find mannanase variants with improved stability during production of the enzyme by fermentation, achieving an improved yield of nondegraded enzyme product. Such variants may be called "stable to degradation" herein.

The mannanase variants of the invention, in one embodiment, provide improved yield of nondegraded product in production and better performance in use.

In one aspect, the present invention provides a mannanase being stable during fermentation and thereby resulting in higher yield of enzyme having sufficient enzymatic activity. The mannanase is at least 75% identical to SEQ ID NO: 2, preferably at least 75% identical to a sequence according to positions 31-490 of SEQ ID NO: 2. The sequence according to positions 31-490 of SEQ ID NO: 2 equals SEQ ID NO: 3.

In one aspect, the invention provides a polynucleotide sequence encoding a mannanase variant according to the invention.

In one aspect, the invention provides a vector comprising the polynucleotide sequence of the invention.

In one aspect, the invention provides a recombinant host cell comprising the polynucleotide of the invention of the invention which enables the host cell to express at least one recombinant mannanase variant according to the invention.

In one aspect, the invention provides a method of expressing a polynucleotide, comprising the steps of (a) providing a host cell comprising a heterologous nucleic acid construct comprising a polynucleotide encoding a mannanase variant according to the invention by introducing the nucleic acid construct comprising the polynucleotide encoding the mannanase variant according to the invention into the host cell;

(b) cultivating the recombinant host cell of step (a) under conditions conductive for the expression of the polynucleotide; and (c) optionally, recovering a protein of interest encoded by the polynucleotide.

In one aspect of the invention, the mannanase variants according to the invention are provided within an enzyme preparation that allows to be flexibly formulated into liquid formulations such as liquid detergent formulations with either one type of enzymes or mixtures of enzymes. "Formulated into" means that an enzyme preparation is added to a liquid formulation.

The enzyme preparation may further comprise other enzyme(s) selected from the group consisting of proteases, amylases, cellulases, lipases, xylanases, mannanases, cutinases, esterases, phytases, DNAses, pectinases, pectate lyases, pectinolytic enzymes, carbohydrases, arabinases, galactanases, xanthanases, xyloglucanases, laccases, peroxidases and oxidases with, as well as suitable additives selected from the group consisting of compounds stabilizing the enzymes comprised such as enzyme stabilizers, and compounds stabilizing the preparation such as preservatives.

Sequences

The sequences used herein are as follows

SEQ ID NO: 1: polynucleotide sequence encoding parent mannanase according to SEQ ID NO: 2:

atgtcaatta ttaagaaagt tccattaata tttctatgtc
tcctaatgtt tgctacttct ctatttattt ttaagcctga
ggtaaaagca gcaactggct tttatgtaaa cggaaacact
ctgtacgatg caacaggtag cccgtttgtt atgaggggaa
ttaaccatgc tcattcttgg tttaaagatg attcttctac
agcaatccct gctatagcga agacaggggc taatactatt
agaatcgtcc tatctgatgg aagccagtat acaaaagatg
atattaatac agtaaaaagt cttatatcct tagctgagaa
gaataacctt attgctattt tagaggtgca tgatgccaca
ggaaacgatg ctgttagctc gttaaacgat gctgttagct
attggattag tattaaagag gctcttattg gaaaagaaga
tagggtctta attaatattg ccaatgaatg gtatggtact
tgggatggtg caagttgggc aagtggctat aaacaggcta
ttccaaagtt aagagatgct ggactcagcc atacattaat
tgtagattcc gcaggttggg gacaatatcc agagtctatc
catcaatatg gtaaagatgt atttaatgct gatccactaa
aaaatacaat gttttctatt catatgtatg aatatgctgg
gggggatgct tccactatta aatcaaatat tgacggagta
ctgaatcagg atcttgcatt aattattggt gaatttggac
ataaacatac gaatggagat gttgatgagg aaacaattat
gagttactca cagcagaaga atgttggttg gttagcttgg
tcttggaaag gtaatggccc cgagtggagt tatttagact -continued tatcaaatga ttgggctgga gataatttaa cctcgtgggg
taatacaatt gtaaatggag ctaatggttt aaaagctact
tctaaaataa gtccagtatt tgatggagga gatcatcctg
gtggttcagg tggaactgaa aatactttgt ataatttcga
aaccgaaaca caaagctgga gtggtggaaa tgtaatggct
ggaccctggt caacgaatga gtgggcatca aaagacaact
attctttaaa agctgatgtt caattaaaca ataattccca
gcattattta tctttaactc aaaaccaaaa tttcagtggg
aaatctcaac taaaggcaac tgtaaagcac gctgattggg
gaaatctagg gaatggaatt aatgcacagt tatatgtgaa
aacagggtca gattggaaat ggtttgatgg tgagagtgta
gaaattaatt cctccaatgg aactatttta actttagatt
tatcatccat ctccgattta aatgacatta aagagattgg
cgtgcagttt atgggctctt cgaaaagcag tggtcaaaca
gctgtatacg ttgacaacgt aacaattcaa taa SEQ ID NO: 2 parent mannanase (490AA including signal sequence) in its one-letter code:

MSIIKKVPLIFLCLLMFATSLFIFKPEVKAATGFYVNGNTLYDATGSPFV
MRGINHAHSWFKDDSSTAIPAIAKTGANTIRIVLSDGSQYTKDDINTVKS
LISLAEKNNLIAILEVHDATGNDAVSSLNDAVSYWISIKEALIGKEDRVL
INIANEWYGTWDGASWASGYKQAIPKLRDAGLSHTLIVDSAGWGQYPESI
HQYGKDVFNADPLKNTMFSIHMYEYAGGDASTIKSNIDGVLNQDLALIIG
EFGHKHTNGDVDEETIMSYSQQKNVGWLAWSWKGNGPEWSYLDLSNDWAG
DNLTSWGNTIVNGANGLKATSKISPVFDGGDHPGGSGGTENTLYNFETET
QSWSGGNVMAGPWSTNEWASKDNYSLKADVQLNNNSQHYLSLTQNQNFSG
KSQLKATVKHADWGNLGNGINAQLYVKTGSDWKWFDGESVEINSSNGTIL
TLDLSSISDLNDIKEIGVQFMGSSKSSGQTAVYVDNVTIQ

SEQ ID NO: 3 mature parent mannanase including linker and CBD (carbohydrate domain) in its one-letter code:

ATGFYVNGNTLYDATGSPFVMRGINHAHSWFKDDSSTAIPAIAKTGANTI
RIVLSDGSQYTKDDINTVKSLISLAEKNNLIAILEVHDATGNDAVSSLND
AVSYWISIKEALIGKEDRVLINIANEWYGTWDGASWASGYKQAIPKLRDA
GLSHTLIVDSAGWGQYPESIHQYGKDVFNADPLKNTMFSIHMYEYAGGDA
STIKSNIDGVLNQDLALIIGEFGHKHTNGDVDEETIMSYSQQKNVGWLAW
SWKGNGPEWSYLDLSNDWAGDNLTSWGNTIVNGANGLKATSKISPVFDGG
DHPGGSGGTENTLYNFETETQSWSGGNVMAGPWSTNEWASKDNYSLKADV
QLNNNSQHYLSLTQNQNFSGKSQLKATVKHADWGNLGNGINAQLYVKTGS
DWKWFDGESVEINSSNGTILTLDLSSISDLNDIKEIGVQFMGSSKSSGQT
AVYVDNVTIQ

DETAILED DESCRIPTION OF THE INVENTION

It is to be understood that as used in the specification and in the claims, “a” or “an” can mean one or more (in the sense of “at least one”), depending upon the context in which it is used.

Further, it will be understood that the term “at least” means that the item or parameter to which the term refers is limited in one direction but open ended in one or more other directions.

As used in the following, the terms “have”, “comprise”, “contain” or “include” or any arbitrary grammatical variations thereof are used in a non-exclusive way. Thus, these terms may both refer to a situation in which, besides the feature introduced by these terms, no further features are present in the entity described in this context and to a situation in which one or more further features are present.

Features introduced by “in one embodiment” or similar expressions are intended to be additional or alternative features, without any restriction regarding alternative embodiments of the invention, without any restrictions regarding the scope of the invention and without any restriction regarding the possibility of combining the features introduced in such way with other additional or alternative or non-additional or alternative features of the invention. The term “may” preferably herein encompasses embodiments.

The term “about” as used herein means that with respect to any number recited after said term an interval accuracy exists within in which a technical effect can be achieved. Accordingly, about as referred to herein, preferably, refers to the precise numerical value or a range around said precise numerical value of ±15%, preferably ±10%, more preferably ±5%, or even more preferably ±3%.

Generally, “enzymes” are catalytically active proteins or polypeptides acting on substrates and converting these into products. This reaction may be called enzymatic conversion herein which typically takes place at the “active site” of an enzyme. Enzymes exerting enzymatic conversion are enzymatically active or have enzymatic activity. Any polypeptide called “enzyme” herein means polypeptides being catalytically active.

The mannanase variants according to the invention have mannan degrading activity and are of the enzyme class EC 3.2.1.78. In one embodiment, mannan degrading activity means degradation of at least one galactomannan. Preferably, at least one galactomannan is characterized by the ratio mannose:galactose of about 1:1, about 2:1, about 3:1, about 4:1, and/or 5:1.

Mannan degrading activity or mannanase activity may be tested according to standard test procedures known in the art. For example: a mannanase to be tested may be applied to 4 mm diameter holes punched out in agar plates comprising 0.2% AZCL galactomannan (carob), i.e. substrate for the assay of endo-1,4-beta-D-mannanase available as I-AZGMA from the company Megazyme (Megazyme's Internet address: world wide web at megazyme.com/Purchase/index.html). Mannan degrading activity may be tested in a liquid assay using carob galactomannan dyed with Remazol Brilliant Blue as described in McCleary, B. V. (1978). Carbohydrate Research, 67 (1), 213-221. Another method for testing mannan degrading activity uses detection of reducing sugars when incubated with substrate such as guar gum or locust bean gum—for reference see Miller, G. L. Use of Dinitrosalicylic Acid Reagent for Determination of Reducing Sugars. Analytical Chemistry 1959; 31:426-428.

Enzymes are polypeptides which are usually identified by polypeptide sequences (also called amino acid sequences herein). Polypeptide sequences may be identified by a SEQ ID NO. which is provided according to the World Intellectual Property Office (WIPO) Standard ST.25 (1998) in the sequence listing accompanying this disclosure, meaning that the amino acids herein are represented using three-letter code with the first letter as a capital or the corresponding one letter.

A polypeptide is usually encoded by a polynucleotide. The polynucleotide usually is identified by a polynucleotide sequence and by a SEQ ID NO. which is provided according to the World Intellectual Property Office (WIPO) Standard ST.25 (1998) in the sequence listing accompanying this disclosure.

A “parent” polypeptide amino acid sequence is the starting sequence for introduction of mutations (e.g. by introducing one or more amino acid substitutions, insertions, deletions, or a combination thereof) to the sequence, resulting in “variants” of the parent polypeptide amino acid sequences. A parent includes: A wild-type polypeptide amino acid sequence or synthetically generated polypeptide amino acid sequence that is used as starting sequence for introduction of (further) changes.

The parent polypeptides for the mannanase variants of this invention may have a polypeptide sequence according to SEQ ID NO: 2 or SEQ ID NO: 3. In one aspect of the invention the parent polypeptide has a sequence according to positions 31-490 of SEQ ID NO: 2. The sequence according to positions 31-490 of SEQ ID NO: 2 equals SEQ ID NO: 3.

A “variant polypeptide” refers to an enzyme that differs from its parent in its amino acid sequence.

Variant polypeptide sequences may be defined by their “sequence identity” when compared to a parent sequence. An enzyme or polypeptide “at least x % identical to SEQ ID NO:X” means an enzyme or polypeptide having a polypeptide sequence which is x % identical when compared to the polypeptide sequence according to SEQ ID NO:X, wherein SEQ ID NO:X means the sequences according to the invention. In one embodiment, SEQ ID NO:X is selected from SEQ ID NO: 2, SEQ ID NO: 3 and SEQ ID NO: 4.

A polynucleotide “at least y % identical to SEQ ID NO:Y” means a polynucleotide having a polynucleotide sequence which is y % identical when compared to the polynucleotide sequence according to SEQ ID NO:Y, which corresponds to SEQ ID NO: 1 herein.

Sequence identity usually is provided as “% sequence identity” or “% identity”. For calculation of sequence identities, in a first step a sequence alignment has to be produced.

According to the invention, the alignment is generated by using the algorithm of Needleman and Wunsch (J. Mol. Biol. (1979) 48, p. 443-453). Preferably, the program “NEEDLE” (The European Molecular Biology Open Software Suite (EMBOSS)) is used for the purposes of the current invention, with using the programs default parameter (polynucleotides: gap open=10.0, gap extend=0.5 and matrix=EDNAFULL; polypeptides: gap open=10.0, gap extend=0.5 and matrix=EBLOSUM62).

After aligning two sequences, in a second step, an identity value is determined from the alignment produced.

In one embodiment, the %-identity is calculated by dividing the number of identical residues by the length of the alignment region which is showing the respective sequence of this invention over its complete length multiplied with 100: %-identity=(identical residues/length of the alignment region which is showing the respective sequence of this invention over its complete length) *100.

Polypeptide

A polypeptide of the invention is at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 2 and wherein the polypeptide has mannan-degrading activity. In one aspect of the invention, the mannanase variant according to the invention is at least 75%, at least 80%, at least 85%, at least 90%, at least 91%, at least 92%, at least 93%, at least 94%, at least 95%, at least 96%, at least 97%, at least 98%, or at least 99% identical to the sequence according to positions 31-490 of SEQ ID NO: 2 or according to SEQ ID NO: 3, and wherein the polypeptide has mannan-degrading activity.

The mannanase variants of the invention may further comprise one or more conservative substitutions, meaning that one amino acid is substituted with a similar amino acid. Similar amino acids according to the invention are defined as follows:

amino acid A is similar to amino acids S; amino acid D is similar to amino acids E and N; amino acid E is similar to amino acids D, K, and Q; amino acid F is similar to amino acids W and Y; amino acid H is similar to amino acids N and Y; amino acid I is similar to amino acids L, M, and V; amino acid K is similar to amino acids E, Q, and R; amino acid L is similar to amino acids I, M, and V; amino acid M is similar to amino acids I, L, and V; amino acid N is similar to amino acids D, H, and S; amino acid Q is similar to amino acids E, K, and R; amino acid R is similar to amino acids K and Q; amino acid S is similar to amino acids A, N, and T; amino acid T is similar to amino acids S; amino acid V is similar to amino acids I, L, and M; amino acid W is similar to amino acids F and Y; amino acid Y is similar to amino acids F, H, and W.

In one embodiment, a mannanase variant according to the invention is a "mature polypeptide" meaning an enzyme in its final form including any post-translational modifications, glycosylation, phosphorylation, truncation, N-terminal modifications, C-terminal modifications, signal sequence deletion. A mature polypeptide can vary depending upon the expression system, vector, promoter, and/or production process. The mature mannanase variant according to the invention may be at least 75% identical to the sequence according to positions 31-490 of SEQ ID NO: 2 or may be at least 75% identical to the sequence according to SEQ ID NO: 3.

The invention provides a polypeptide at least 75% identical to the sequence according to SEQ ID NO: 2 or SEQ ID NO: 3 comprising one or more amino acid substitutions selected from N341, F346, T348, E349, S352, G356, and D379, wherein the numbering is according to SEQ ID NO: 2. At least one amino acid substitution may be selected from N341F, F346T, T348S/R/N/M/G, E349T/S/G/D, S352N/G, G356Y/V/T/Q/H/C, and D379V.

In one aspect of the invention, a mannanase variant according to the invention, comprises one or more conservative amino acid substitutions at the following positions T32, N37, F61, 180, Y90, T91, K99, S100, V125, L150, D179, S183, Y196, D206, D229, N258, I323, N345, V358, S370, N383, N384, Q423, F435, D459, N461S, I463 and V482 preferably selected from at least one of the following substitutions: T32S, N37S, F61Y, 180V, Y90W, T91S, K99R, S100N, V125I, L150I, D179N, S183N, Y196F, D206E, D229N, N258D, I323 L, N345D, V358I, S370A, N383S, N384S, Q423K, F435Y, D459N, N461S, I463V and V482L, wherein the mannanase variant is at least 75% identical to the sequence according to SEQ ID NO: 2 or SEQ ID NO: 3, and wherein the numbering is according to SEQ ID NO: 2. The mannanase variants according to the invention may comprise combinations of substitutions selected from T32S, T91S, K99R, S100N, V125I, D179N, S183N, Y196F, D206E, N258D, V358I, S370A, Q423K, D459N, N461S, and V482L. The mannanase variants according to the invention may comprise combinations of substitutions selected from T32S, N37S, F61Y, 180V, Y90W, K99R, S100N, V125I, L150I, D179N, S183N, Y196F, D206E, D229N, and I323L. Preferably, the mannanase variants according to the invention comprise one or more conservative amino acid substitutions selected from N37S, F61Y, I80V, Y90W, T91S, L150I, D229N, N258D, I323L, N345D, V358I, S370A, N383S, N384S, Q423K, F435Y, D459N, N461S, I463V, and V482L, wherein the mannanase variant is at least 75% identical to the sequence according to SEQ ID NO:2, or SEQ ID NO: 3, and wherein the numbering is according to SEQ ID NO: 2.

In one embodiment, the mannanase variants according to the invention comprise one or more amino acid substitutions at the following positions: N39T, T45N, D64Q, S133D, E140S, S168D, A173V, Q202N, S305D, H332D, G335D, A360G, A365V, D372G, Q381N, S391Y, F398L, K433T, E438G, I449T, and K475N, wherein the mannanase variant is at least 75% identical to the sequence according to SEQ ID NO: 2, or SEQ ID NO: 3, and wherein the numbering is according to SEQ ID NO: 2. The mannanase variants according to the invention may comprise combinations of substitutions selected from S133D, S168D, A173V, Q202N, S305D, H332D, G335D, A365V, D372G, Q381N, S391Y, E438G, and K475N. The mannanase variants according to the invention may comprise combinations of substitutions selected from N39T, T45N, D64Q, S133D, E140S, and S168D. Preferably, the mannanase variants according to the invention comprise one or more amino acid substitutions selected from A360G and I449T, wherein the mannanase variant is at least 75% identical to the sequence according to SEQ ID NO: 2 or SEQ ID NO: 3, and wherein the numbering is according to SEQ ID NO: 2.

In one embodiment, the mannanase variants according to the invention comprise one or more conserved amino acid regions within their polypeptide sequence. Conserved amino acid regions herein are characterized in a number of consecutive amino acids being not mutated, wherein the number of consecutive amino acids is 3-10, 4-10, 5 to 10, 6, 7, 8, 9, or 10. One or more conserved amino acid regions may be selected from G76-A77-N78-T79, R81-V83-L84, E115-V116-H117-D118, Y134-W135-1136, A154-N155-E156-W157, A191-G192-W193-G194-Q195, F218-S219-I220-H221-M222-Y223-E224-Y225-A226-G227, N236-I237-D238, 1249-G250-E251-F252-G253, G259-D260-V261-D262-E263, and G276-W277-L278-A279-W280, and wherein the numbering is according to SEQ ID NO: 2.

In one aspect of the invention, the mannanase variant according to the invention has improved fermentation stability when compared to the parent enzyme.

Fermentation stability according to the invention is the proportion of mannanase enzyme consisting of catalytic domain, linker, and CBD produced by fermentation vs mannanase enzyme that has been endogenously truncated.

Improved fermentation stability herein means that the fermentations stability of a mannanase variant according to the invention is at least 1.5-fold, at least 1.6-fold, at least 2-fold when compared to the parent enzyme.

In one embodiment, fermentation stability means fermentation stability when expressed in bacterial host cell, preferably *Bacillus* host cell, more preferably in *Bacillus subtilis* host cell.

In one embodiment, fermentation stability means fermentation stability at a fermentation temperature in the range of 35° C. to 45° C., preferably at a temperature of 37° C.

In one embodiment, the mannanase variant having improved fermentation stability is a polypeptide at least 75% identical to SEQ ID NO: 2 having amino acid substitutions in at least two or more of the positions selected from N341F, F346T, T348S/R/N/M/G, E349T/S/G/D, S352N/G, G356Y/V/T/Q/H/C, and D379V, wherein the numbering is according to SEQ ID NO: 2. In one embodiment, the mannanase having improved fermentation stability is a polypeptide at least 75% identical to SEQ ID NO: 2 having (a) one or more amino acid substitutions at a position selected from T348N/G, S352N, and D379V, preferably in combination with (b) one or more amino acid substitutions selected from N341F, F346T, T348S/R/M, E349T/S/G/D, S352G, and G356Y/V/T/Q/H/C, wherein amino acid substitutions as defined under (b) are not present when at a corresponding position as defined in (a) a substitution is present, and wherein the numbering is according to SEQ ID NO: 2, and wherein the polypeptide has mannan-degrading activity Polynucleotide The invention relates to a polynucleotide encoding a mannanase variant according to the invention. A polynucleotide encodes a polypeptide at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 2. In one aspect of the invention, the polynucleotide encodes a polypeptide at least 75%, at least 80%, at least 85%, at least 90%, at least 91%, at least 92%, at least 93%, at least 94%, at least 95%, at least 96%, at least 97%, at least 98%, or at least 99% identical to the sequence according to SEQ ID NO: 3. The polynucleotide of the invention may have a sequence at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 1.

A polynucleotide according to the invention encodes a mannanase variant according to the invention which is at least 75% identical to the sequence according to SEQ ID NO: 2 or SEQ ID NO: 3 comprising one or more amino acid substitutions selected from N341F, F346T, T348S/R/N/M/G, E349T/S/G/D, S352N/G, G356Y/V/T/Q/H/C, and D379V, wherein the numbering is according to SEQ ID NO: 2.

In one embodiment, a polynucleotide encoding a mannanase variant according to the invention, encodes one or more conservative amino acid substitutions at the following positions: T32S, N37S, F61Y, 180V, Y90W, T91S, K99R, S100N, V125I, L150I, D179N, S183N, Y196F, D206E, D229N, N258D, I323L, N345D, V358I, S370A, N383S, N384S, Q423K, F435Y, D459N, N461S, I463V, and V482L, wherein the mannanase variant is at least 75% identical to the sequence according to SEQ ID NO: 2 or SEQ ID NO: 3, and wherein the numbering is according to SEQ ID NO: 2. The polynucleotide encoding a mannanase variant according to the invention may encode combinations of amino acid substitutions selected from T32S, T91S, K99R, S100N, V125I, D179N, S183N, Y196F, D206E, N258D, V358I, S370A, Q423K, D459N, N461S, and V482L. The polynucleotide encoding a mannanase variant according to the invention may encode combinations of substitutions selected from T32S, N37S, F61Y, 180V, Y90W, K99R, S100N, V125I, L150I, D179N, S183N, Y196F, D206E, D229N, and I323L. Preferably, the polynucleotide encoding a mannanase variant according to the invention encodes one or more conservative amino acid substitutions selected from N37S, F61Y, 180V, Y90W, T91S, L150I, D229N, N258D, I323L, N345D, V358I, S370A, N383S, N384S, Q423K, F435Y, D459N, N461S, I463V, V482L, wherein the mannanase variant is at least 75% identical to the sequence according to SEQ ID NO: 2 or SEQ ID NO: 3, and wherein the numbering is according to SEQ ID NO: 2.

In one embodiment, the polynucleotide encoding a mannanase variant according to the invention, encodes one or more amino acid substitutions at the following positions: N39T, T45N, D64Q, S133D, E140S, S168D, A173V, Q202N, S305D, H332D, G335D, A360G, A365V, D372G, Q381N, S391Y, F398L, K433T, E438G, I449T, and K475N, wherein the mannanase variant is at least 75% identical to the sequence according to SEQ ID NO: 2 or SEQ ID NO: 3, and wherein the numbering is according to SEQ ID NO: 2. The polynucleotide encoding a mannanase variant according to the invention may encode combinations of amino acid substitutions selected from S133D, S168D, A173V, Q202N, 5305D, H332D, G335D, A365V, D372G, Q381N, S391Y, E438G, and K475N. The polynucleotide encoding a mannanase variant according to the invention may encode combinations of substitutions selected from N39T, T45N, D64Q, S133D, E140S, and S168D. Preferably, the polynucleotide encoding a mannanase variant according to the invention encodes one or more amino acid substitutions selected from A360G and I449T, wherein the mannanase variant is at least 75% identical to the sequence according to SEQ ID NO: 2, or SEQ ID NO: 3, and wherein the numbering is according to SEQ ID NO: 2.

In one embodiment, the mannanase variants according to the invention comprise one or more conserved amino acid regions within their polypeptide sequence. Conserved amino acid regions herein are characterized in a number of consecutive amino acids being not mutated, wherein the number of consecutive amino acids is 3-10, 4-10, 5 to 10, 6, 7, 8, 9, or 10. One or more conserved amino acid regions may be selected from G76-A77-N78-T79, R81-V83-L84, E115-V116-H117-D118, Y134-W135-I136, A154-N155-E156-W157, A191-G192-W193-G194-Q195, F218-S219-I220-H221-M222-Y223-E224-Y225-A226-G227, N236-I237-D238, I249-G250-E251-F252-G253, G259-D260-V261-D262-E263, and G276-W277-L278-A279-W280, and wherein the numbering is according to SEQ ID NO: 2.

Method to Improve Fermentation Stability

The invention, in one aspect, relates to a method to increase fermentation stability of a mannanase which is at least 75% identical to SEQ ID NO: 2 or SEQ ID NO: 3, by the step of introducing one or more amino acid substitution at an amino acid position selected from N341F, F346T, T348S/R/N/M/G, E349T/S/G/D, S352N/G, G356Y/V/T/Q/H/C, and D379V, wherein the numbering is according to SEQ ID NO: 2. Preferably, the fermentation stability of the mannanase variant is increased by at least about 50% when compared to the respective parent enzyme.

In one embodiment, the method to increase fermentation stability of a mannanase which is at least 75% identical to SEQ ID NO: 2 or SEQ ID NO: 3 includes the step of introducing one or more amino acid substitution at an amino acid position selected from N341F, F346T, T348S/R/N/M/G, E349T/S/G/D, S352N/G, G356Y/T/H/C, and D379V, wherein the numbering is according to SEQ ID NO: 2. Preferably, the fermentation stability of the mannanase variant is increased by at least 100% when compared to the respective parent enzyme.

In one embodiment, the method to increase fermentation stability of a mannanase which is at least 75% identical to SEQ ID NO: 2 or SEQ ID NO: 3 includes the step of introducing one or more amino acid substitution at an amino acid position selected from N341F, F346T, T348S/R/N/M/G, E349S/G/D, S352G, G356Y/T/C, and D379V, wherein the numbering is according to SEQ ID NO: 2. Preferably, the fermentation stability of the mannanase variant is increased by at least 150% when compared to the respective parent enzyme.

In one embodiment, the method to increase fermentation stability of a mannanase which is at least 75% identical to SEQ ID NO: 2 or SEQ ID NO: 3 includes the step of introducing one or more amino acid substitution at an amino acid position selected from N341F, F346T, T348N/M/G, E349S/G/D, S352G and D379V, wherein the numbering is according to SEQ ID NO: 2. Preferably, the fermentation stability of the mannanase variant is increased by at least 200% when compared to the respective parent enzyme.

Production of Mannanase

The present invention refers to a method of producing a mannanase variant according to the invention, comprising the steps of (a) providing a host cell comprising a heterologous nucleic acid construct comprising a polynucleotide encoding the mannanase variant according to the invention by introducing the nucleic acid construct comprising the polynucleotide encoding the mannanase variant according to the invention into the host cell;
(b) cultivating the recombinant host cell of step (a) under conditions conductive for the expression of the polynucleotide; and
(c) optionally, recovering a protein of interest encoded by the polynucleotide.

The present invention also refers to a method of expressing a mannanase variant according to the invention, comprising the steps of (a) providing a host cell comprising a heterologous nucleic acid construct comprising a polynucleotide encoding the mannanase variant according to the invention by introducing the nucleic acid construct comprising the polynucleotide encoding the mannanase variant according to the invention into the host cell;
(b) cultivating the recombinant host cell of step (a) under conditions conductive for the expression of the polynucleotide; and
(c) optionally, recovering a protein of interest encoded by the polynucleotide.

A polynucleotide encoding a polypeptide may be "expressed". The term "expression" or "gene expression" means the transcription of a specific gene or specific genes or specific nucleic acid construct. The term "expression" or "gene expression" in particular means the transcription of a gene or genes or genetic construct into structural RNA (e.g., rRNA, tRNA) or mRNA with or without subsequent translation of the latter into a protein. The process includes transcription of DNA and processing of the resulting mRNA product.

Nucleic acid construct herein means a nucleic acid molecule, either single- or double-stranded which is isolated from a naturally occurring gene or is modified to contain segments of nucleic acids in a manner that would not otherwise exist in nature or which is synthetic, which comprises one or more control sequences. The term "control sequences" means nucleic acid sequences necessary for expression of a polynucleotide encoding a mannanase of the present invention. Each control sequence may be native or foreign to the polynucleotide encoding the variant or native or foreign to each other. Such control sequences include, but are not limited to, a leader, polyadenylation sequence, pro-peptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Industrial production of enzymes usually is done by using expression systems. "Expression system" may mean a host microorganism, expression hosts, host cell, production organism, or production strain and each of these terms can be used interchangeably. In one embodiment, the expression host is selected from the group consisting of: a bacterial expression system, a yeast expression system, a fungal expression system, and a synthetic expression system. The expression host may be a wildtype cell or a recombinant cell, preferably it is a recombinant cell. "Wild-type cells" herein means cells prior to a certain modification. The term "recombinant cell" (also called "genetically modified cell" herein) refers to a cell which has been genetically altered, modified or engineered such it that exhibits an altered, modified or different genotype as compared to the wild-type cell which it was derived from. The "recombinant cell" may comprise an exogenous polynucleotide encoding a certain protein or enzyme and therefore may express said protein or enzyme.

In one embodiment, the invention is directed to a recombinant host cell comprising a polynucleotide encoding the mannanase as described herein. The host cell may be any cell useful in the recombinant production of a variant including prokaryotes and eukaryotes.

Examples of expression hosts include but are not limited to: *Aspergillus niger, Aspergillus* oryzae, *Hansenula polymorpha, Thermomyces lanuginosus, Fusarium oxysporum, Fusarium* heterosporum, *Escherichia coli, Bacillus*, preferably selected from *Bacillus subtilis, Bacillus* pumilus, and *Bacillus licheniformis, Pseudomonas*, preferably *Pseudomonas fluorescens, Pichia pastoris* (also known as Komagataella phaffii), *Myceliopthora thermophila* (C1), *Themothelomyces thermophilus, Schizosaccharomyces pombe, Trichoderma*, preferably *Trichoderma reesei*, and *Saccharomyces*, preferably *Saccharomyces cerevisiae*. The mannanase variant according to the invention may be produced using host cell originating from the microorganisms listed above.

In one embodiment, the bacterial expression system is selected from *E. coli, Bacillus, Pseudomonas*, and *Streptomyces*. In one embodiment, the yeast expression system is selected from *Candida, Pichia, Saccharomyces*, and *Schizosaccharomyces*. In one embodiment, the fungal expression system is selected from *Penicillium, Aspergillus, Fusarium, Myceliopthora, Rhizo mucor, Rhizopus, Thermomyces*, and *Trichoderma*.

Preferably, the recombinant host cell of the invention is a Gram-positive bacteria including but not limited to, *Bacillus, Clostridium, Enterococcus, Geobacillus, Lactobacillus, Lactococcus, Oceanobacillus, Staphylococcus, Streptococcus*, and *Streptomyces*. More preferably, the host cell is a

*Bacillus* cell, more preferably selected from the group of *Bacillus alkalophius, Bacillus amyloliquefaciens, Bacillus brevis, Bacillus circulans, Bacillus clausii, Bacillus coagulans, Bacillus firmus, Bacillus jautus, Bacillus lentus, Bacillus licheniformis, Bacillus megaterium, Bacillus pumilus, Bacillus stearothermophilus, Bacillus subtilis*, and *Bacillus thuringiensis*. Most preferred, the *Bacillus* cell is selected from *Bacillus subtilis, Bacillus pumilus, Bacillus licheniformis*, and *Bacillus lentus*. In one embodiment, the *Bacillus* cell is a *Bacillus subtilis* cell.

The invention provides a fermentation method for producing a fermentation product, comprising the steps of a) providing a recombinant host cell according to the invention, and b) cultivating the recombinant host cell under conditions allowing for the expression of polynucleotide encoding a mannanase of the invention.

The term "heterologous" (or exogenous or foreign or recombinant) in the context of polynucleotides and polypeptides is defined herein as:

(a) not native to the host cell; or (b) native to the host cell but structural modifications, e.g., deletions, substitutions, and/or insertions, are included as a result of manipulation of the DNA of the host cell by recombinant DNA techniques to alter the native sequence; or (c) native to the host cell but expression is quantitatively altered or expression is directed from a genomic location different from the native host cell as a result of manipulation of the DNA of the host cell by recombinant DNA techniques, e.g., a stronger promoter.

Preferably, "Heterologous" Herein Means "not Native to the Host Cell".

The invention in one aspect relates to a host cell, preferably *Bacillus*, expressing a polynucleotide which encodes a polypeptide at least 75% identical to SEQ ID NO:2 having amino acid substitutions in one or more of the positions selected from N341, F346, T348, E349, S352, G356, and D379, wherein the numbering is according to SEQ ID NO: 2 and wherein the mannanase has improved fermentation stability when compared to the parent enzyme. At least one amino acid substitution may be selected from N341F, F346T, T348S/R/N/M/G, E349T/S/G/D, S352N/G, G356Y/V/T/Q/H/C, and D379V.

In one embodiment, the host cell expressing a mannanase variant according to the invention having improved fermentation stability comprises a polynucleotide encoding a mannanase variant which is at least 75% identical to SEQ ID NO: 2 having amino acid substitutions in at least two or more of the positions selected from N341F, F346T, T348S/R/N/M/G, E349T/S/G/D, S352N/G, G356Y/V/T/Q/H/C, and D379V, wherein the numbering is according to SEQ ID NO: 2. In one embodiment, the mannanase having improved fermentation stability is a polypeptide at least 75% identical to SEQ ID NO: 2 having (a) one or more amino acid substitutions at a position selected from T348N/G, S352N, D379V and combinations thereof, preferably in combination with (b) at least one amino acid substitution selected from N341F, F346T, T348S/R/M, E349T/S/G/D, S352G, and G356Y/V/T/Q/H/C, wherein amino acid substitutions as defined under (b) are not present when at a corresponding position as defined in (a) a substitution is present, and wherein the numbering is according to SEQ ID NO: 2, and wherein the polypeptide has mannan-degrading activity In one embodiment, the invention is directed to a genetic construct comprising a polynucleotide encoding the mannanase of the invention. "Genetic Construct" or "expression cassette" or "expression construct" as used herein, is a DNA molecule composed of at least one polynucleotide sequence of the invention to be expressed, operably linked to one or more control sequences (at least to a promoter) as described herein. Typically, the expression cassette comprises three elements: a promoter sequence, an open reading frame, and a 3' untranslated region that, in eukaryotes, usually contains a polyadenylation site.

Additional regulatory elements may include transcriptional as well as translational enhancers. An intron sequence may also be added to the 5' untranslated region (UTR) or in the coding sequence to increase the amount of the mature message that accumulates in the cytosol. The expression cassette may be part of a vector or may be integrated into the genome of a host cell and replicated together with the genome of its host cell. The expression cassette usually is capable of increasing or decreasing expression.

The term "vector" as used herein comprises any kind of construct suitable to carry foreign polynucleotide sequences for transfer to another cell, or for stable or transient expression within a given cell. The term "vector" as used herein encompasses any kind of cloning vehicles, such as but not limited to plasmids, phagemids, viral vectors (e.g., phages), bacteriophage, baculoviruses, cosmids, fosmids, artificial chromosomes, or and any other vectors specific for specific hosts of interest. Low copy number or high copy number vectors are also included. Foreign polynucleotide sequences usually comprise a coding sequence which may be referred to herein as "gene of interest". The gene of interest may comprise introns and exons, depending on the kind of origin or destination of host cell.

A vector as used herein may provide segments for transcription and translation of a foreign polynucleotide upon transformation into a host cell or host cell organelles. Such additional segments may include regulatory nucleotide sequences, one or more origins of replication that is required for its maintenance and/or replication in a specific cell type, one or more selectable markers, a polyadenylation signal, a suitable site for the insertion of foreign coding sequences such as a multiple cloning site etc. One example is when a vector is required to be maintained in a bacterial cell as an episomal genetic element (e.g. plasmid or cosmid molecule). Nonlimiting examples of suitable origins of replication include the f1-ori and colE1. A vector either replicates without integrating into the genome of a host cell, e.g. as a plasmid in a bacterial host cell, or integrates parts or all of its DNA into the genome of the host cell and thus lead to replication and expression of its DNA.

Foreign nucleic acid may be introduced into a vector by means of cloning. Cloning may mean that by cleavage of the vector (e.g. within the multiple cloning site) and the foreign polynucleotide by suitable means and methods (e.g., restriction enzymes), fitting structures within the individual nucleic acids may be created that enable the controlled fusion of said foreign nucleic add and the vector. Once introduced into the vector, the foreign nucleic acid comprising a coding sequence is introduced (transformed, transduced, transfected, etc.) into a host cell or host cell organelles. A cloning vector may be chosen suitable for expression of the foreign polynucleotide sequence in the host cell or host cell organelles.

The term "introduction" or "transformation" as referred to herein encompasses the transfer of an exogenous polynucleotide into a host cell, irrespective of the method used for transfer. That is, the term "transformation" as used herein is independent from vector, shuttle system, or host cell, and it not only relates to the polynucleotide transfer method of transformation as known in the art (cf., for example, Sambrook, J. et al. (1989) Molecular Cloning: A Laboratory Manual, 2nd Ed., Cold Spring Harbor Laboratory Press, Cold Spring Harbor, N.Y.), but it encompasses any further kind polynucleotide transfer methods such as, but not limited to, transduction or transfection. Plant tissue capable of subsequent clonal propagation, whether by organogenesis or embryogenesis, may be transformed with a genetic construct and a whole plant regenerated therefrom. The particular tissue chosen will vary depending on the clonal propagation systems available for, and best suited to, the particular species being transformed. In one embodiment of the invention, a vector is used for transformation of a host cell.

The polynucleotide of the invention may be transiently or stably introduced into a host cell, preferably a *Bacillus* host cell, and may be maintained non-integrated, for example, as a plasmid. "Stable transformation" means that the transformed cell or cell organelle passes the nucleic acid comprising the foreign coding sequence on to the next generations of the cell or cell organelles. Usually stable transformation is due to integration of nucleic acid comprising a foreign coding sequence into the chromosomes or as an episome (separate piece of nuclear DNA). "Transient transformation" means that the cell or cell organelle once transformed expresses the foreign nucleic acid sequence for a certain time— mostly within one generation. Usually transient transformation is due to nucleic acid comprising a foreign nucleic acid sequence is not integrated into the chromosomes or as an episome. Alternatively, it is integrated into the host genome.

Enzymes are usually produced as a liquid concentrate, frequently derived from a fermentation broth. "Liquid enzyme concentrate" herein means any liquid enzyme-comprising product comprising at least one enzyme. "Liquid" in the context of enzyme concentrate is related to the physical appearance at 20° C. and 101.3 kPa.

The liquid enzyme concentrate may result from dissolution of solid enzyme in solvent. The solvent may be selected from water and an organic solvent. A liquid enzyme concentrate resulting from dissolution of solid enzyme in solvent may comprise amounts of enzyme up to the saturation concentration.

Dissolution herein means, that solid compounds are liquified by contact with at least one solvent. Dissolution means complete dissolution of a solid compound until the saturation concentration is achieved in a specified solvent, wherein no phase-separation occurs.

In one aspect of the invention, the enzyme concentrate may be essentially free of water, meaning that no significant amounts of water are present. Non-significant amounts of water herein means, that the enzyme concentrate comprises less than 25%, less than 20%, less than 15%, less than 10%, less than 7%, less than 5%, less than 4%, less than 3%, less than 2% by weight water, all relative to the total weight of the enzyme concentrate, or no water. In one embodiment, enzyme concentrate free of water means that the enzyme concentrate does not comprise significant amounts of water but does comprise organic solvents in amounts of 30-80% by weight, relative to the total weight of the enzyme concentrate.

Liquid enzyme concentrates comprising water may be called "aqueous enzyme concentrates". In one embodiment, aqueous enzyme concentrates are enzyme-comprising solutions, wherein solid enzyme product has been dissolved in water. In one embodiment "aqueous enzyme concentrate" means enzyme-comprising products resulting from enzyme production by fermentation.

Fermentation means the process of cultivating recombinant cells which express the desired enzyme in a suitable nutrient medium allowing the recombinant host cells to grow and express the desired protein. At the end of the fermentation, fermentation broth usually is collected and further processed, wherein the fermentation broth comprises a liquid fraction and a solid fraction. Depending on whether the enzyme has been secreted into the liquid fraction or not, the desired protein or enzyme may be recovered from the liquid fraction of the fermentation broth or from cell lysates. Recovery of the desired enzyme uses methods known to those skilled in the art. Suitable methods for recovery of proteins or enzymes from fermentation broth include but are not limited to collection, centrifugation, filtration, extraction, and precipitation.

Aqueous enzyme concentrates resulting from fermentation may comprise amounts of enzyme in the range of 0.1% to 40% by weight, or 0.5% to 30% by weight, or 1% to 25% by weight, or 3% to 25% by weight, or 5% to 25% by weight, all relative to the total weight of the enzyme concentrate.

Aqueous enzyme concentrates resulting from fermentation may comprise water in amounts of more than about 50% by weight, more than about 60% by weight, more than about 70% by weight, or more than about 80% by weight, all relative to the total weight of the enzyme concentrate. Aqueous enzyme concentrates resulting from fermentation, in one embodiment comprise water in amounts in the range of about 50% to 80% by weight, or about 60% to 70% by weight, all relative to the total weight of the enzyme concentrate. Aqueous enzyme concentrates which result from fermentation, may comprise residual components such as salts originating from the fermentation medium, cell debris originating from the production host cells, metabolites produced by the production host cells during fermentation. In one embodiment, residual components may be comprised in liquid enzyme concentrates in amounts less than 30% by weight, less than 20% by weight less, than 10% by weight, or less than 5% by weight, all relative to the total weight of the aqueous enzyme concentrate.

Enzymes tend to lose enzymatic activity if remaining in an aqueous environment and so it is conventional practice to convert it to an anhydrous form: aqueous concentrates may be lyophilized or spray-dried e.g. in the presence of a carrier material to form aggregates. Usually, solid enzyme products need to be "dissolved" prior to use. To stabilize enzymes in liquid products enzyme inhibitors are usually employed, preferably reversible enzyme inhibitors, to inhibit enzyme activity temporarily until the enzyme inhibitor is released.

Use of the Mannanase of the Invention

The invention relates to the use of a mannanase according to the invention, to degrade mannan in a mannan-containing material.

Mannan degradation, in one embodiment, means degradation of at least one galactomannan. Preferably, at least one galactomannan is characterized by the ratio mannose:galactose of about 1:1, about 2:1, about 3:1, about 4:1, and/or 5:1.

The mannanase variants according to the invention preferably exert mannan degrading activity at a temperature selected from 560° C., 540° C., and 525° C.

Enzyme Preparation

An enzyme preparation of the invention is preferably liquid. "Liquid" in the context of enzyme preparation is related to the physical appearance at 20° C. and 101.3 kPa.

The enzyme preparation of the invention comprises a liquid enzyme concentrate comprising at least one mannanase variant according to the invention. An enzyme preparation of the invention comprises only components effective in stabilizing the enzyme preparation or the enzyme comprised therein, e.g. selected from at least one enzyme stabilizer, at least one compound stabilizing the liquid enzyme preparation as such, and at least one solvent.

In one aspect, the invention provides a liquid enzyme preparation comprising a mannanase variant according to the invention which is at least 75% identical to SEQ ID NO: 2, preferably a mannanase at least 75% identical to a sequence according to SEQ ID NO: 3, at least one compound stabilizing the liquid enzyme preparation as such, at least one solvent, and optionally at least one enzyme stabilizer.

Liquid enzyme preparations of the invention are preferably free from surfactants. In one embodiment, free from surfactants means, that no actively added surfactants are comprised in enzyme preparations of the invention. This means that enzyme preparations of the invention may comprise surfactants which result from the fermentation process from which the enzyme concentrate originates (as a by-product).

Liquid enzyme preparations of the invention are preferably free from complexing agents. In one embodiment, free from complexing agents means, that no actively added complexing agents are comprised in enzyme preparations of the invention. This means that enzyme preparations of the invention may comprise complexing agents which result from the fermentation process from which the enzyme concentrate originates (as a by-product).

In one embodiment, liquid enzyme preparations of the invention are free from surfactants and free from complexing agents.

Compounds Stabilizing the Liquid Enzyme Preparation as Such

Compounds stabilizing the liquid enzyme preparation as such means any compound except enzyme stabilizers needed to establish storage stability of a liquid preparation in amounts effective to ensure the storage stability.

Storage stability in the context of liquid preparations to those skilled in the art usually includes aspects of appearance of the product and uniformity of dosage.

Appearance of the product is influenced by the pH of the product and by the presence of compounds such as preservatives, antioxidants, viscosity modifiers, emulsifiers etc.

Uniformity of dosage is usually related to the homogeneity of a product.

Inventive enzyme preparations may be alkaline or exhibit a neutral or slightly acidic pH value. The enzyme preparation may have a pH in the range of 5-12, preferably in the range of 6-11, more preferably in a range selected from 6-10, 7-9, and 7.5-8.5.

The liquid enzyme preparation of the invention may comprise at least one preservative. Preservatives are added in amounts effective in preventing microbial contamination of the liquid enzyme preparation, preferably the aqueous enzyme preparation.

The invention in one aspect pertains to a method of preserving an aqueous enzyme preparation according to the invention against microbial contamination or growth, which method comprises addition of an antimicrobial agent selected from the group consisting of 2-phenoxyethanol in a concentration of 0.01% to 5%, more preferably 0.1% to 2%, glutaraldehyde in a concentration of 2 ppm to 5000 ppm, more preferably 10 ppm to 2000 ppm, 2-bromo-2-nitropropane-1,3-diol in a concentration of 5 ppm to 5000 ppm, more preferably 20 ppm to 1000 ppm, formic acid in acid form or as its salt in a concentration of 0.01% to 3%, more preferably 0.05% to 0.5% and 4,4'-dichloro 2-hydroxydiphenyl ether in a concentration of 0.001% to 1%, more preferably 0.002% to 0.6% to an aqueous enzyme concentrate comprising a mannanase variant according to the invention.

In one embodiment, liquid enzyme preparations of the invention are free from preservatives, meaning that preservatives are comprised in amounts less than 1 ppm. In one embodiment, "free from preservatives" means, that no actively added preservatives are comprised in enzyme preparations of the invention. This means that enzyme preparations may comprise preservatives which result from the fermentation process from which the enzyme concentrate originates (as a by-product).

Solvents

In one embodiment, the inventive enzyme preparation is aqueous, comprising water in amounts in the range of 5% to 95% by weight, in the range of 5% to 30% by weight, in the range of 5% to 25% by weight, in the range of 30% to 80% by weight, or in the range of 20% to 70% by weight, all relative to the total weight of the enzyme preparation.

In one embodiment, the enzyme preparation of the invention comprises at least one organic solvent selected from ethanol, n-propanol, iso-propanol, n-butanol, iso-butanol, sec.-butanol, ethylene glycol, propylene glycol, 1,3-propane diol, butane diol, glycerol, diglycol, propyl diglycol, butyl diglycol, hexylene glycol, ethylene glycol methyl ether, ethylene glycol ethyl ether, ethylene glycol propyl ether, and phenoxyethanol, preferred are ethanol, isopropanol or propylene glycol. Further, the enzyme preparation of the invention may comprise at least one organic solvent selected from compounds such as 2-butoxyethanol, isopropyl alcohol, and d-limonene.

In a preferred embodiment, enzyme preparations of the invention comprise at least one water miscible organic solvent. Water miscibility in this context means the property of the organic solvent to mix in all proportions in water, forming a homogeneous solution. Preferably, at least one water miscible solvent is selected from ethanol, isopropanol or 1,2-propylene glycol.

In one embodiment, enzyme preparations of the invention comprise (a) amounts of water in the range of about 20% to 50% and (b) at least one organic solvent in amounts in the range of 30% to 60% by weight, or in amounts in the range of 45% to 55% by weight, all relative to the total weight of the enzyme preparation.

In one embodiment, enzyme preparations of the invention comprise organic solvents in amounts in the range of 0% to 20% by weight relative to the total weight of the enzyme preparation. Preferably, enzyme preparations of the invention comprise amounts of water in the range of about 30% to 80% by weight and at least one organic solvent in amounts of less than 10% by weight, less than 5% by weight, or less than 1% by weight, all relative to the total weight of the enzyme preparation.

In one embodiment, the enzyme preparation comprises water in amounts in the range of 5% to 15% by weight and no significant amounts of organic solvent, for example 1% by weight or less, all relative to the total weight of the enzyme preparation.

Enzyme Stabilizer

Stabilization of an enzyme herein relates to stability in the course of time (e.g. storage stability), thermal stability, pH stability, and chemical stability. The term “enzyme stability” herein preferably relates to the retention of enzymatic activity as a function of time e.g. during storage or operation. Enzyme stabilizers stabilize an enzyme in liquid, preferably aqueous environment, meaning that it reduced or avoids loss of enzymatic activity in the course of time.

In one embodiment, at least one enzyme, preferably at least one mannanase variant according to the invention, is stabilized by the presence of water-soluble sources of calcium and/or magnesium ions within the enzyme preparation. In one embodiment, at least one enzyme stabilizer is selected from polyols or water-soluble salts.

Polyols may be selected from polyols containing from 2 to 6 hydroxyl groups. Suitable examples include glycol, 1,2-propane diol, 1,2-butane diol, 1,4-butane diol, 1,2-pentandiol, 1,6-hexane diol, ethylene glycol, hexylene glycol, glycerol, sorbitol, mannitol, erythriol, glucose, fructose, and lactose.

Water-soluble salts may be selected from salts like NaCl or KCl, and alkali salts of lactic acid and formic acid.

In an embodiment of the invention, water-soluble salts may be selected from water-soluble sources of zinc (II), calcium (II) and/or magnesium (II) ions in the finished compositions that provide such ions to the enzymes, as well as other metal ions (e.g. barium (II), scandium (II), iron (II), manganese (II), aluminum (III), Tin (II), cobalt (II), copper (II), Nickel (II), and oxovanadium (IV)). Preferably, the water-soluble salt is selected from $CaCl_2$ and $MgCl_2$.

The enzyme preparation may comprise one or more other enzyme(s) than a mannanase variant according to the invention, which are selected from the group consisting of proteases, amylases, cellulases, lipases, xylanases, mannanases different from the mannanase variants according to the invention, cutinases, esterases, phytases, DNAses, pectinases, pectate lyases, pectinolytic enzymes, carbohydrases, arabinases, galactanases, xanthanases, xyloglucanases, laccases, peroxidases and oxidases.

In one embodiment, the enzyme preparation further comprises a protease, preferably a serine protease (EC 3.4.21), more preferably a subtilisin EC 3.4.21.62; and/or a lipase, preferable a triacylglycerol lipase (EC 3.1.1.3), more preferably a *Thermomyces lanuginosus* lipase. Preferably said enzyme preparations comprise at least one enzyme stabilizer selected from boron-containing compounds, polyols, peptide aldehydes, other stabilizers, and mixtures thereof.

A boron-containing compound may be selected from boric acid or its derivatives and from boronic acid or its derivatives such as aryl boronic acids or its derivatives, from salts thereof, and from mixtures thereof. Boric acid herein may be called orthoboric acid.

In one embodiment, a boron-containing compound is selected from the group consisting of aryl boronic acids and its derivatives. In one embodiment, a boron-containing compound is selected from the group consisting of benzene boronic acid (BBA) which is also called phenyl boronic acid (PBA), derivatives thereof, and mixtures thereof.

In one embodiment a phenyl-boronic acid derivative is selected from the group consisting of 4-formyl phenyl boronic acid (4-FPBA), 4-carboxy phenyl boronic acid (4-CPBA), 4-(hydroxymethyl) phenyl boronic acid (4-HMPBA), and p-tolylboronic acid (p-TBA).

In one embodiment, the enzyme preparations, preferably those additionally comprising a subtilisin protease, comprises about 0.1-2% by weight relative to the total weight of the enzyme preparation of at least one boron-containing compound. Preferably, the enzyme preparation comprises about 0.15-1%, or 0.2-0.5%, or about 0.3% by weight relative to the total weight of the enzyme preparation of at least one boron-containing compound. More preferably, the enzyme preparation comprises about 0.3% by weight relative to the total weight of the enzyme preparation of 4-FPBA.

In one embodiment, at least one enzyme stabilizer is selected from peptide stabilizer. At least one peptide stabilizer may be selected from a compound of formula (D):

(D)

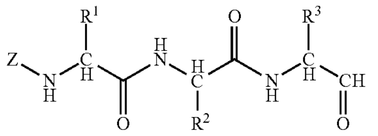

$R^1$, $R^2$, $R^3$, $R^4$, $R^5$ and Z within formula (b) are defined as follows:

- $R^1$, $R^2$ and Ware each independently selected from the group consisting of hydrogen, optionally substituted $C_{1-8}$ alkyl, optionally substituted $C_{2-6}$ alkenyl, optionally substituted $C_{1-8}$ alkoxy, optionally substituted 3- to 12-membered cycloalkyl, and optionally substituted 6- to 10-membered aryl; or wherein each $R^1$, $R^2$ and $R^3$ is independently selected as $—(CH_2)_3—$ which is also attached to the nitrogen atom of —NH—C(H)— so that —N—C(H)$R^{1,2\ or\ 3}$— forms a 5-membered heterocyclic ring;
- $R^4$ and $R^5$ are each independently selected from the group consisting of hydrogen, optionally substituted $C_{1-8}$ alkyl, optionally substituted $C_{2-6}$ alkenyl, optionally substituted $C_{1-8}$ alkoxy, optionally substituted $C_{1-4}$ acyl, optionally substituted $C_{1-8}$ alkyl phenyl (e.g. benzyl), and optionally substituted 6- to 10-membered aryl; or wherein $R^4$ and $R^5$ are joined to form an optionally substituted 5- or 6-membered ring;
- Z is selected from hydrogen, an N-terminal protection group, and one or more amino acid residues optionally comprising an N-terminal protection group.

In a preferred embodiment, the peptide stabilizer according to formula (D) is characterized in

- $R^1$ is a group such that NH—CHR$^1$—CO is an L or D-amino acid residue of Val, $R^2$ is a group such that NH—CHR$^2$—CO is an L or D-amino acid residue of Ala, and $R^3$ is a group such that NH—CHR$^3$—CO is an L or D-amino acid residue of Leu;

and

- the N-terminal protection group Z is selected from benzyloxycarbonyl (Cbz), p-methoxybenzyl carbonyl (MOZ), benzyl (Bn), benzoyl (Bz), p-methoxybenzyl (PMB), p-methoxyphenyl (PMP), formyl, acetyl (Ac), methyloxy, alkoxycarbonyl, methoxycarbonyl, fluorenylmethyloxycarbonyl (Fmoc), or tert-butyloxycarbonyl (Boc); preferably, the N-terminal protection group Z is benzyloxycarbonyl (Cbz).

In one embodiment, the enzyme preparations, preferably those additionally comprising a subtilisin protease, comprises about 0.1-2% by weight relative to the total weight of the enzyme preparation of at least one peptide stabilizer.

Preferably, the enzyme preparation comprises about 0.15-1%, or 0.2-0.5%, or about 0.3% by weight relative to the total weight of the enzyme preparation of at least one peptide stabilizer.

Mannanase Application

The invention in one aspect relates to the use of the mannanase variants according to the invention to be formulated into detergent formulations such as I&I and homecare formulations for laundry and hard surface cleaning, wherein at least one mannanase variant according to the invention and at least one detergent component are mixed in no specified order in one or more steps with one or more detergent components.

In one embodiment, the formulation has a pH in the range of 6-11, more preferably in a range selected from 6-10, 7-12, 7-9, 8-12, 8-10 and 7.5-8.5. In one embodiment, the formulation is a detergent formulation, preferably a liquid detergent formulation.

A detergent formulation according to the invention comprises at least one mannanase of the invention and one or more detergent component(s). The component(s) chosen depend on the desired washing or cleaning application and/or physical form of the detergent formulation.

The term “detergent component” is defined herein to mean any types of ingredient, which is suitable for detergent formulation, such as surfactants, building agents, polymers, bleaching systems. Any component(s) known in the art acknowledging their known characteristics are suitable detergent component(s) according to the invention. Detergent components in one embodiment means components which provide washing or cleaning performance, or which effectively aid the processing (maintain physical characteristics during processing, storage and use; e.g. rheology modifiers, hydrotropes, desiccants) when present in effective amounts.

Usually, a detergent formulation is a complex formulation of more than two detergent components.

Detergent components may have more than one function in the final application of a detergent formulation, therefore any detergent component mentioned in the context of a specific function herein, may also have another function in the final application of a detergent formulation. The function of a specific detergent component in the final application of a detergent formulation usually depends on its amount within the detergent formulation, i.e. the effective amount of a detergent component.

The term “effective amount” includes amounts of individual components to provide effective stain removal and effective cleaning conditions (e.g. pH, quantity of foaming), amounts of certain components to effectively provide optical benefits (e.g. optical brightening, dye transfer inhibition), and amounts of certain components to effectively aid the processing (maintain physical characteristics during processing, storage and use; e.g. rheology modifiers, hydrotropes, desiccants).

In one embodiment, the detergent formulation according to the invention is a formulation of more than two detergent components, wherein at least one component is effective in stain removal, at least one component is effective in providing the optimal cleaning conditions, and at least one component is effective in maintaining the physical characteristics of the detergent.

Individual detergent components and usage in detergent formulation are known to those skilled in the art. Suitable detergent components comprise inter alia surfactants, builders, polymers, alkaline, bleaching systems, fluorescent whitening agents, suds suppressors and stabilizers, hydrotropes, and corrosion inhibitors. Further examples are described e.g. in “complete Technology Book on Detergents with Formulations (Detergent Cake, Dishwashing Detergents, Liquid & Paste Detergents, Enzyme Detergents, Cleaning Powder & Spray Dried Washing Powder)”, Engineers India Research Institute (EIRI), 6th edition (2015). Another reference book for those skilled in the art may be “Detergent Formulations Encyclopedia”, Solverchem Publications, 2016.

The mannanase variants according to the invention preferably exert mannan degrading activity at a washing or cleaning temperature selected from 560° C., 540° C., and 525° C. Mannan degrading activity in the context of washing or cleaning herein relates to its ability to remove mannan-containing stains.

In one aspect, the present invention provides a method of removing mannan comprising stains by the steps of contacting at least one mannan comprising stain with a mannanase of the invention. The mannanase has mannan degrading activity at a pH in the range of 5-12 or 6-11, more preferably a pH in the range of 6-10 or 7-9 or 7-12 or 8-12 or 8-10, and most preferably at a pH in the range of 7.5-8.5. At said pH the mannanase shows wash performance on mannan comprising stains. Preferably, the method is a method of removing mannan comprising stains at temperatures 560° C., preferably in the range of about 5-60° C., preferably in the range of about 5-40° C., more preferably in the range of about 10-40° C.

EXAMPLES

Example 1: Expression and Purification of Mannanase Variants

The genes were synthesized and cloned into *Bacillus* expression vector by GenScript (New Jersey, USA). The constructs were received from GenScript as sequence-confirmed plasmid DNA and transformed into *Bacillus subtilis*. 5 μL of plasmid DNA, 20-200 ng/μL was added to 500 μL freshly prepared *Bacillus subtilis* competent cells and incubated at 37° C. for 3.5 hours. Cells were subsequently plated onto LB+50 ug/mL Kanamycin agar plates and grown overnight at 37° C. To confirm the mannanase expression in *Bacillus subtilis*, the resulting colonies were screened via colony PCR and sequencing. Prior to PCR, each colony was lysed in buffer containing 20 mM DTT and 0.5 mg/mL Proteinase K at 55° C. for 5 minutes followed by 95° C. for 6 minutes. 20 μL PCR reactions using 1 μL of lysed cells and TaKaRa Ex Taq (TaKaRa Cat # RR001) polymerase were performed as follows: initial denaturation for 3 minutes at 98° C., 30 cycles of denaturation, annealing, and extension for 10 seconds at 95° C., 30 seconds at 55° C., and 2.5 minutes at 72° C., respectively. A final extension for 5 minutes at 72° C. completed the PCR reactions. Expression of the mannanase was done for example in microtiter plate format. Fermentations were carried out at 30° C. and under 1000 rpm of agitation for approximately 48 hours. The final fermentation broth was centrifuged at 2500×g for 15 mins at 4° C. to obtain the cell-free supernatant. Protein quantification was estimated using an automated capillary gel electrophoresis device; LabChip® GX II with an HT Protein Express LabChip® and an HT Protein Express Reagent Kit (PerkinElmer, USA). Determination of protein purity and quantitation was carried out using the Regular Sensitivity HT Protein Express 200 assay and analysis performed using the LabChip®GX Reviewer 5.3 software. Molecular weight determinations were performed either via the LabChip software, which uses bracketing ladders of protein standards (as part of the HT Protein Express Reagent Kit) to assign MW of the peaks and quantitation, or by using known protein standards and the "Titer" function within the instrument analysis software, or by using the LabChip derived peak area of a set of protein standards with known concentrations, to generate a standard curve and resulting quantitation for protein of interest.

Example 2: Expression of Mannanases Expression

Expression of the mannanase was completed in 384-well deep well plate. Fermentations were carried out at 37° C. and under 1000 rpm of agitation for approximately 48 hours. The final fermentation broth was centrifuged at 2500×g for 15 mins at 4° C. to obtain the cell-free supernatant.

Protein quantification was estimated using an automated capillary gel electrophoresis device; LabChip® GX II with an HT Protein Express LabChip® and an HT Protein Express Reagent Kit (PerkinElmer, USA). Determination of protein purity and quantitation was carried out using the Regular Sensitivity HT Protein Express 200 assay and analysis performed using the LabChip®GX Reviewer 5.3 software. Molecular weight determinations were performed either via the LabChip software, which uses bracketing ladders of protein standards (as part of the HT Protein Express Reagent Kit) to assign MW of the peaks and quantitation, or by using known protein standards and the "Titer" function within the instrument analysis software, or by using the LabChip derived peak area of a set of protein standards with known concentrations, to generate a standard curve and resulting quantitation for protein of interest.

Fermentation stability of mannanase variants was determined by calculating the quantity of full length enzyme as well as the percent full length mannanase (quantity of full length divided by the summed total of the full length mannanase and observed degradation product(s) multiplied by 100).

TABLE Ex2 fermentation stability of mannanase variants with single point mutations as indicated in the table when compared to the parent enzyme

| parent | substitution | Quantity of full length | % of full length |
|---|---|---|---|
| parent | — | 1 | 1 |
| N341 | F | 1.67 | 3.62 |
| F346 | T | 1.97 | 3.32 |
| T348 | S | 1.52 | 2.57 |
| | R | 1.55 | 2.65 |
| | N | 2.31 | 7.17 |
| | M | 1.57 | 3.17 |
| | G | 2.78 | 6.39 |
| | T | 1.66 | 2.89 |
| | Q | 1.41 | 1.51 |
| | H | 1.80 | 2.23 |
| E349 | T | 1.63 | 2.25 |
| | S | 1.92 | 3.89 |
| | G | 2.52 | 5.24 |
| E349 | D | 1.79 | 3.78 |
| S352 | N | 1.49 | 2.09 |
| | G | 2.76 | 5.76 |
| G356 | Y | 1.59 | 2.79 |
| | V | 1.46 | 1.65 |
| | C | 1.52 | 2.72 |
| D379 | V | 3.65 | 6.12 |

The invention claimed is:

1. A mannanase variant comprising an amino acid sequence having at least 90% sequence identity to the full-length amino acid sequence of SEQ ID NO: 2 or SEQ ID NO: 3, comprising at least one amino acid substitution selected from N341F, F346T, T348S/R/N/M/G, E349T/S/G/D, S352N/G, G356Y/V/T/Q/H/C, and D379V, wherein the numbering is according to SEQ ID NO: 2.

2. A polynucleotide encoding the mannanase variant of claim 1.

3. An expression construct comprising the polynucleotide according to claim 2.

4. A host cell comprising the polynucleotide according to claim 2.

5. A method of expressing a mannanase variant according to claim 1, comprising the steps of (a) providing a host cell comprising a heterologous nucleic acid construct comprising a polynucleotide encoding the mannanase variant according to claim 1 by introducing the heterologous nucleic acid construct comprising the polynucleotide encoding the mannanase variant according to claim 1 into the host cell to produce a recombinant host cell;

(b) cultivating the recombinant host cell of step (a) under conditions conductive for the expression of the polynucleotide; and (c) optionally, recovering a protein of interest encoded by the polynucleotide.

6. A liquid enzyme preparation comprising the mannanase according to claim 1, at least one compound stabilizing the liquid enzyme preparation, at least one solvent, and optionally at least one enzyme stabilizer.

7. A detergent formulation comprising at least one mannanase variant according to claim 1 and one or more detergent component(s).

8. The mannanase variant of claim 1, wherein the mannanase variant comprises an amino acid sequence having at least 90% sequence identity to the full-length amino acid sequence of to SEQ ID NO: 2, comprising at least one amino acid substitution selected from N341F, F346T, T348S/R/N/M/G, E349T/S/G/D, S352N/G, G356Y/V/T/Q/H/C, and D379V, wherein the numbering is according to SEQ ID NO: 2.

9. The mannanase variant of claim 1, wherein the mannanase variant comprises an amino acid sequence having at least 95% sequence identity to the full-length amino acid sequence of to SEQ ID NO: 2, comprising at least one amino acid substitution selected from N341F, F346T, T348S/R/N/M/G, E349T/S/G/D, S352N/G, G356Y/V/T/Q/H/C, and D379V, wherein the numbering is according to SEQ ID NO: 2.

10. The mannanase variant of claim 1, wherein the mannanase variant comprises an amino acid sequence having at least 90% sequence identity to the full-length amino acid sequence of SEQ ID NO: 3, comprising at least one amino acid substitution selected from N341F, F346T, T348S/R/N/M/G, E349T/S/G/D, S352N/G, G356Y/V/T/Q/H/C, and D379V, wherein the numbering is according to SEQ ID NO: 2.

11. The mannanase variant of claim 8, wherein the mannanase variant comprises at least two amino acid substitutions selected from N341F, F346T, T348S/R/N/M/G, E349T/S/G/D, S352N/G, G356Y/V/T/Q/H/C, and D379V, wherein the numbering is according to SEQ ID NO: 2.

12. The mannanase variant of claim 10, wherein the mannanase variant comprises at least two amino acid substitutions selected from N341F, F346T, T348S/R/N/M/G, E349T/S/G/D, S352N/G, G356Y/V/T/Q/H/C, and D379V, wherein the numbering is according to SEQ ID NO: 2.

13. The mannanase variant of claim 1, wherein the mannanase variant comprises an amino acid sequence having at least 95% sequence identity to the full-length amino acid sequence of SEQ ID NO: 3, comprising at least one amino acid substitution selected from N341F, F346T, T348S/R/N/M/G, E349T/S/G/D, S352N/G, G356Y/V/T/Q/H/C, and D379V, wherein the numbering is according to SEQ ID NO: 2.

14. The liquid enzyme preparation of claim 6, wherein at least one compound stabilizing the liquid enzyme preparation is a preservative.

* * * * *

SEQUENCE LISTING

```
<160> NUMBER OF SEQ ID NOS: 3

<210> SEQ ID NO 1
<211> LENGTH: 1473
<212> TYPE: DNA
<213> ORGANISM: Unknown
<220> FEATURE:
<223> OTHER INFORMATION: Sequence was obtained from environmental
      sample.

<400> SEQUENCE: 1

atgtcaatta ttaagaaagt tccattaata tttctatgtc tcctaatgtt tgctacttct     60

ctatttattt ttaagcctga ggtaaaagca gcaactggct tttatgtaaa cggaaacact    120

ctgtacgatg caacaggtag cccgtttgtt atgaggggaa ttaaccatgc tcattcttgg    180

tttaaagatg attcttctac agcaatccct gctatagcga agacaggggc taatactatt    240

agaatcgtcc tatctgatgg aagccagtat acaaaagatg atattaatac agtaaaaagt    300

cttatatcct tagctgagaa gaataacctt attgctattt tagaggtgca tgatgccaca    360

ggaaacgatg ctgttagctc gttaaacgat gctgttagct attggattag tattaaagag    420

gctcttattg gaaaagaaga tagggtctta attaatattg ccaatgaatg gtatggtact    480

tgggatggtg caagttgggc aagtggctat aaacaggcta ttccaaagtt aagagatgct    540

ggactcagcc atacattaat tgtagattcc gcaggttggg gacaatatcc agagtctatc    600

catcaatatg gtaaagatgt atttaatgct gatccactaa aaaatacaat gttttctatt    660

catatgtatg aatatgctgg gggggatgct tccactatta aatcaaatat tgacggagta    720
```

-continued ctgaatcagg atcttgcatt aattattggt gaatttggac ataaacatac gaatggagat 780
gttgatgagg aaacaattat gagttactca cagcagaaga atgttggttg gttagcttgg 840
tcttggaaag gtaatggccc cgagtggagt tatttagact tatcaaatga ttgggctgga 900
gataatttaa cctcgtgggg taatacaatt gtaaatggag ctaatggttt aaaagctact 960
tctaaaataa gtccagtatt tgatggagga gatcatcctg gtggttcagg tggaactgaa 1020
aatactttgt ataatttcga aaccgaaaca caaagctgga gtggtggaaa tgtaatggct 1080
ggaccctggt caacgaatga gtgggcatca aaagacaact attctttaaa agctgatgtt 1140
caattaaaca ataattccca gcattattta tctttaactc aaaaccaaaa tttcagtggg 1200
aaatctcaac taaaggcaac tgtaaagcac gctgattggg gaaatctagg gaatggaatt 1260
aatgcacagt tatatgtgaa aacagggtca gattggaaat ggtttgatgg tgagagtgta 1320
gaaattaatt cctccaatgg aactatttta actttagatt tatcatccat ctccgattta 1380
aatgacatta aagagattgg cgtgcagttt atgggctctt cgaaaagcag tggtcaaaca 1440
gctgtatacg ttgacaacgt aacaattcaa taa 1473

<210> SEQ ID NO 2
<211> LENGTH: 490
<212> TYPE: PRT
<213> ORGANISM: Unknown
<220> FEATURE:
<223> OTHER INFORMATION: Parent protein (including signal peptide), encoded by Seq-ID 1. Signal peptide is pos 1 to 30.
<220> FEATURE:
<221> NAME/KEY: misc_feature
<222> LOCATION: (1)..(30)
<223> OTHER INFORMATION: Signal Peptide

<400> SEQUENCE: 2

Met Ser Ile Ile Lys Lys Val Pro Leu Ile Phe Leu Cys Leu Leu Met
1 5 10 15

Phe Ala Thr Ser Leu Phe Ile Phe Lys Pro Glu Val Lys Ala Ala Thr
20 25 30

Gly Phe Tyr Val Asn Gly Asn Thr Leu Tyr Asp Ala Thr Gly Ser Pro
35 40 45

Phe Val Met Arg Gly Ile Asn His Ala His Ser Trp Phe Lys Asp Asp
50 55 60

Ser Ser Thr Ala Ile Pro Ala Ile Ala Lys Thr Gly Ala Asn Thr Ile
65 70 75 80

Arg Ile Val Leu Ser Asp Gly Ser Gln Tyr Thr Lys Asp Asp Ile Asn
85 90 95

Thr Val Lys Ser Leu Ile Ser Leu Ala Glu Lys Asn Asn Leu Ile Ala
100 105 110

Ile Leu Glu Val His Asp Ala Thr Gly Asn Asp Ala Val Ser Ser Leu
115 120 125

Asn Asp Ala Val Ser Tyr Trp Ile Ser Ile Lys Glu Ala Leu Ile Gly
130 135 140

Lys Glu Asp Arg Val Leu Ile Asn Ile Ala Asn Glu Trp Tyr Gly Thr
145 150 155 160

Trp Asp Gly Ala Ser Trp Ala Ser Gly Tyr Lys Gln Ala Ile Pro Lys
165 170 175

Leu Arg Asp Ala Gly Leu Ser His Thr Leu Ile Val Asp Ser Ala Gly
180 185 190

Trp Gly Gln Tyr Pro Glu Ser Ile His Gln Tyr Gly Lys Asp Val Phe
195 200 205

-continued

Asn Ala Asp Pro Leu Lys Asn Thr Met Phe Ser Ile His Met Tyr Glu
210 215 220

Tyr Ala Gly Gly Asp Ala Ser Thr Ile Lys Ser Asn Ile Asp Gly Val
225 230 235 240

Leu Asn Gln Asp Leu Ala Leu Ile Ile Gly Glu Phe Gly His Lys His
245 250 255

Thr Asn Gly Asp Val Asp Glu Glu Thr Ile Met Ser Tyr Ser Gln Gln
260 265 270

Lys Asn Val Gly Trp Leu Ala Trp Ser Trp Lys Gly Asn Gly Pro Glu
275 280 285

Trp Ser Tyr Leu Asp Leu Ser Asn Asp Trp Ala Gly Asp Asn Leu Thr
290 295 300

Ser Trp Gly Asn Thr Ile Val Asn Gly Ala Asn Gly Leu Lys Ala Thr
305 310 315 320

Ser Lys Ile Ser Pro Val Phe Asp Gly Gly Asp His Pro Gly Gly Ser
325 330 335

Gly Gly Thr Glu Asn Thr Leu Tyr Asn Phe Glu Thr Glu Thr Gln Ser
340 345 350

Trp Ser Gly Gly Asn Val Met Ala Gly Pro Trp Ser Thr Asn Glu Trp
355 360 365

Ala Ser Lys Asp Asn Tyr Ser Leu Lys Ala Asp Val Gln Leu Asn Asn
370 375 380

Asn Ser Gln His Tyr Leu Ser Leu Thr Gln Asn Gln Asn Phe Ser Gly
385 390 395 400

Lys Ser Gln Leu Lys Ala Thr Val Lys His Ala Asp Trp Gly Asn Leu
405 410 415

Gly Asn Gly Ile Asn Ala Gln Leu Tyr Val Lys Thr Gly Ser Asp Trp
420 425 430

Lys Trp Phe Asp Gly Glu Ser Val Glu Ile Asn Ser Ser Asn Gly Thr
435 440 445

Ile Leu Thr Leu Asp Leu Ser Ser Ile Ser Asp Leu Asn Asp Ile Lys
450 455 460

Glu Ile Gly Val Gln Phe Met Gly Ser Ser Lys Ser Ser Gly Gln Thr
465 470 475 480

Ala Val Tyr Val Asp Asn Val Thr Ile Gln
485 490

<210> SEQ ID NO 3
<211> LENGTH: 460
<212> TYPE: PRT
<213> ORGANISM: Unknown
<220> FEATURE:
<223> OTHER INFORMATION: Mature parent protein,
encoded by Seq-ID 1 pos 91 to 1470.

<400> SEQUENCE: 3

Ala Thr Gly Phe Tyr Val Asn Gly Asn Thr Leu Tyr Asp Ala Thr Gly
1 5 10 15

Ser Pro Phe Val Met Arg Gly Ile Asn His Ala His Ser Trp Phe Lys
20 25 30

Asp Asp Ser Ser Thr Ala Ile Pro Ala Ile Ala Lys Thr Gly Ala Asn
35 40 45

Thr Ile Arg Ile Val Leu Ser Asp Gly Ser Gln Tyr Thr Lys Asp Asp
50 55 60

Ile Asn Thr Val Lys Ser Leu Ile Ser Leu Ala Glu Lys Asn Asn Leu

-continued

```
65                  70                  75                  80

Ile Ala Ile Leu Glu Val His Asp Ala Thr Gly Asn Asp Ala Val Ser
                85                  90                  95

Ser Leu Asn Asp Ala Val Ser Tyr Trp Ile Ser Ile Lys Glu Ala Leu
            100                 105                 110

Ile Gly Lys Glu Asp Arg Val Leu Ile Asn Ile Ala Asn Glu Trp Tyr
        115                 120                 125

Gly Thr Trp Asp Gly Ala Ser Trp Ala Ser Gly Tyr Lys Gln Ala Ile
    130                 135                 140

Pro Lys Leu Arg Asp Ala Gly Leu Ser His Thr Leu Ile Val Asp Ser
145                 150                 155                 160

Ala Gly Trp Gly Gln Tyr Pro Glu Ser Ile His Gln Tyr Gly Lys Asp
                165                 170                 175

Val Phe Asn Ala Asp Pro Leu Lys Asn Thr Met Phe Ser Ile His Met
            180                 185                 190

Tyr Glu Tyr Ala Gly Gly Asp Ala Ser Thr Ile Lys Ser Asn Ile Asp
        195                 200                 205

Gly Val Leu Asn Gln Asp Leu Ala Leu Ile Ile Gly Glu Phe Gly His
    210                 215                 220

Lys His Thr Asn Gly Asp Val Asp Glu Glu Thr Ile Met Ser Tyr Ser
225                 230                 235                 240

Gln Gln Lys Asn Val Gly Trp Leu Ala Trp Ser Trp Lys Gly Asn Gly
                245                 250                 255

Pro Glu Trp Ser Tyr Leu Asp Leu Ser Asn Asp Trp Ala Gly Asp Asn
            260                 265                 270

Leu Thr Ser Trp Gly Asn Thr Ile Val Asn Gly Ala Asn Gly Leu Lys
        275                 280                 285

Ala Thr Ser Lys Ile Ser Pro Val Phe Asp Gly Gly Asp His Pro Gly
    290                 295                 300

Gly Ser Gly Gly Thr Glu Asn Thr Leu Tyr Asn Phe Glu Thr Glu Thr
305                 310                 315                 320

Gln Ser Trp Ser Gly Gly Asn Val Met Ala Gly Pro Trp Ser Thr Asn
                325                 330                 335

Glu Trp Ala Ser Lys Asp Asn Tyr Ser Leu Lys Ala Asp Val Gln Leu
            340                 345                 350

Asn Asn Asn Ser Gln His Tyr Leu Ser Leu Thr Gln Asn Gln Asn Phe
        355                 360                 365

Ser Gly Lys Ser Gln Leu Lys Ala Thr Val Lys His Ala Asp Trp Gly
    370                 375                 380

Asn Leu Gly Asn Gly Ile Asn Ala Gln Leu Tyr Val Lys Thr Gly Ser
385                 390                 395                 400

Asp Trp Lys Trp Phe Asp Gly Glu Ser Val Glu Ile Asn Ser Ser Asn
                405                 410                 415

Gly Thr Ile Leu Thr Leu Asp Leu Ser Ser Ile Ser Asp Leu Asn Asp
            420                 425                 430

Ile Lys Glu Ile Gly Val Gln Phe Met Gly Ser Ser Lys Ser Ser Gly
        435                 440                 445

Gln Thr Ala Val Tyr Val Asp Asn Val Thr Ile Gln
    450                 455                 460
```